United States Patent
Ponzini

Patent Number: 5,331,708
Date of Patent: Jul. 26, 1994

[54] INTERDENTAL TOOTH-BRUSH

[75] Inventor: Eligio Ponzini, Lazzate, Italy

[73] Assignee: Ponzini S.p.A., Lazzate, Italy

[21] Appl. No.: 45,238

[22] Filed: Apr. 12, 1993

[51] Int. Cl.$^5$ .................... A46B 3/08; A46B 3/18
[52] U.S. Cl. .................... 15/167.1; 15/111; 15/145; 15/206
[58] Field of Search .................... 15/167.1, 105, 111, 15/145, 176.1, 176.4, 176.5, 176.6

[56] References Cited

U.S. PATENT DOCUMENTS

| | | | |
|---|---|---|---|
| 3,559,226 | 2/1971 | Burns | 15/206 X |
| 4,222,143 | 9/1980 | Tarrson | 15/105 |
| 4,319,377 | 3/1982 | Tarrson | 15/111 |
| 4,780,923 | 11/1988 | Schultheiss | 15/111 |
| 5,005,246 | 4/1991 | Yen-Hui | 15/111 |
| 5,027,467 | 7/1991 | Tarrson et al. | 15/167.1 |
| 5,029,358 | 7/1991 | Zimmerman | 15/167.1 |

FOREIGN PATENT DOCUMENTS 0311937 4/1989 European Pat. Off. .

Primary Examiner—Timothy F. Simone
Assistant Examiner—Patrick F. Brinson
Attorney, Agent, or Firm—Young & Thompson

[57] ABSTRACT

An interdental tooth-brush includes a support bar (1) with a transversal hole (2a) at one end, a small brush stick (3) with a filiform projection (3a) apt to engage into the transversal hole (2a), and a retention device to fix the projection (3a) into the transversal hole (2a) in an interchangeable manner. The transversal hole (2a) is formed into a support head (2) provided at the end of the support bar (1). This support head (2) has a protuberance projecting through a slot (4a) of a cap (4) fitted onto the support head (2). The cap (4), having two diametrically opposite slots (4a, 4b), is axially slidable between a position of release, in which both slots (4a, 4b) are aligned with the transversal hole (2a), and a locking position, in which the rear slot (4b) is axially offset with respect to the hole (2a).

2 Claims, 2 Drawing Sheets

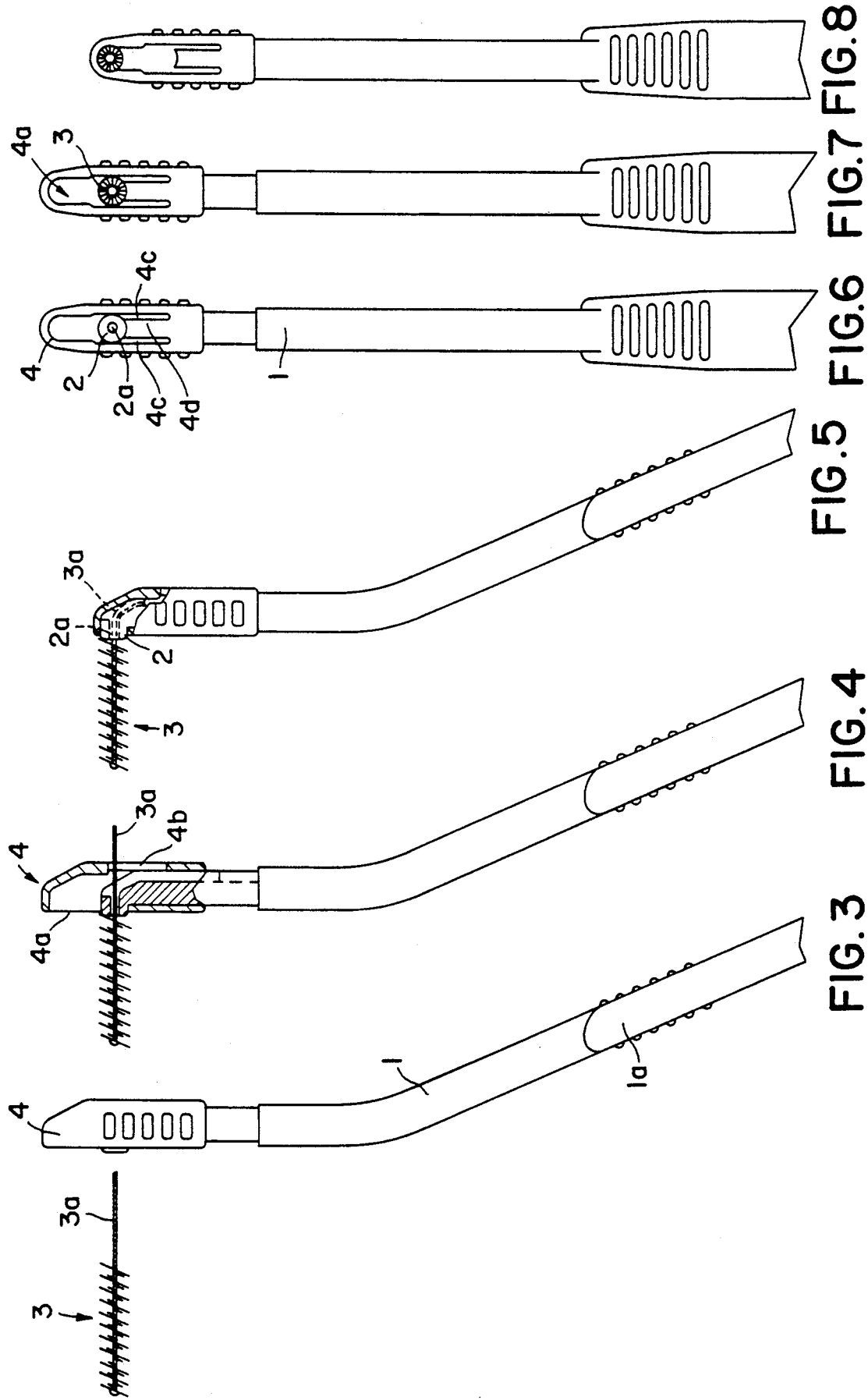

INTERDENTAL TOOTH-BRUSH

BACKGROUND OF THE INVENTION

The present invention concerns an interdental tooth-brush of improved structure.

As known, interdental tooth-brushes are at present widely spread on the market and they generally consist of a suitably shaped support bar, at the free end of which there is mounted a small replaceable brush stick.

Since, for evident reasons of oral hygiene as well as for practical reasons, said small brush stick should be appropriately thrown away quite often and replaced by a new one, it is important for it to be mounted on and removed from the shaped support bar in a very simple and quick way.

For this purpose, it is known to construct the brush stick in the form of a thin braided wire, from which radially project a plurality of single bristles, generally of synthetic material. Said braided wire stick thus comprises a main portion, carrying the bristles for the required cleaning operations, and a tail portion with no bristles, by which it is applied onto the shaped support bar. The brush stick is applied by inserting its tail portion into a transversal hole at the end of the support bar, folding it along said bar and locking it thereon by suitable means.

In a known construction—for example according to U.S. Pat. No. 4,319,377 and U.S. Pat. No. 4,222,143—said locking means consist of an annular bush, by which said tail portion is fixed into an axial retention slot formed at the end of the support bar. The drawback of such locking means lies however in the fact that the bush may slip out of the support bar—for instance when removing the brush stick—and get lost.

The European Patent Publication No. 311,937 provides for a slidable locking bush, which cannot slip off and get lost because of the presence of stop pins. Nevertheless, in this case, the brush stick is mounted by way of a block incorporating the tail portion of the braided wire, whereby the locking bush does not have to bend said braided wire.

According to another known solution, the locking is obtained by means of a half-bush, hinged onto the support bar and covering laterally said folded tail portion of the brush stick. This system prevents the locking means from accidentally slipping out; nevertheless, the half-bush is not apt to ensure a very reliable retention and, furthermore, it comprises sharp edges which can cause trouble to the user when cleaning his or her teeth.

SUMMARY OF THE INVENTION

The object of the present invention is to propose an interdental tooth-brush eliminating the drawbacks of known devices, particularly as it comprises locking means which positively retain the brush stick, which cannot slip out of the support bar, and which have a rounded shape with no sharp edges. This object is reached—in an interdental tooth-brush of the aforementioned type, comprising a support bar with a transversal hole at one end, a small brush stick with a filiform projection apt to engage into said transversal hole, and retention means to fix said projection of the brush stick into said transversal hole in an interchangeable manner—due to the fact that said retention means consist of a cap having two diametrically opposite slots, that said transversal hole is formed into a support head slightly projecting through the front slot of the cap, and that this latter element is fitted onto the end of the support bar, axially slidable between a position of release, in which both slots are aligned with said transversal hole, and a locking position in which the rear slot is axially offset in respect of said hole, in this second position a cavity being formed between the cap and said support head to house and retain the filiform projection of the brush stick in a bent position.

BRIEF DESCRIPTION OF THE DRAWINGS

Further characteristics and advantages of the tooth-brush according to the present invention will anyhow be more evident from the following detailed description of a preferred embodiment thereof, given by way of example and illustrated on the accompanying drawings, in which:

FIGS. 3, 4 and 5 are partial side views, with some parts removed, of the upper part of the tooth-brush, showing three successive mounting steps of the brush stick; and FIGS. 6, 7 and 8 are front views of the tooth-brush, showing the three mounting steps of the previous three figures.

DESCRIPTION OF THE PREFERRED EMBODIMENT

Figure 1:
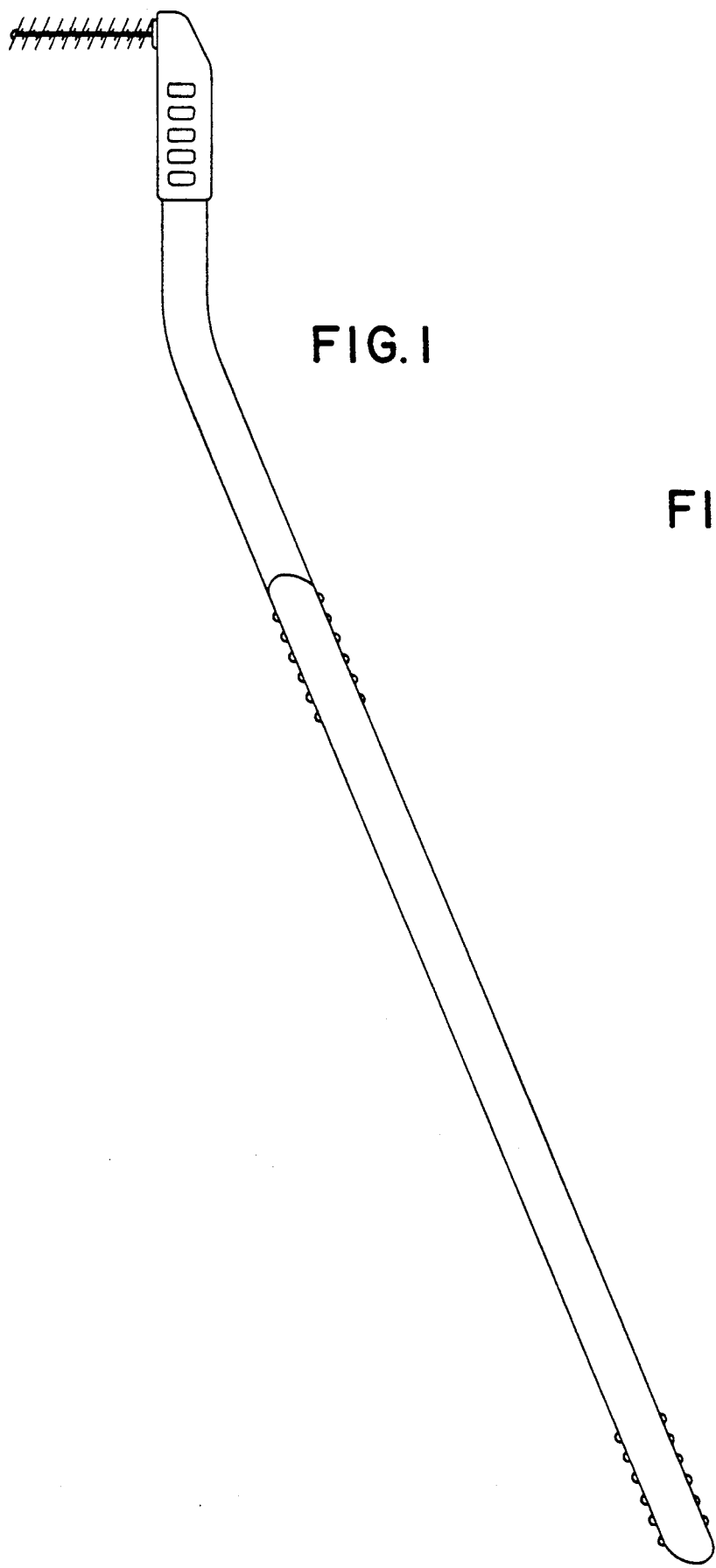
FIGS. 1 and 2 are a side view and, respectively, a front view of the tooth-brush according to the invention.

As shown, the tooth-brush according to the invention comprises a conventional support bar 1 with handgrip 1a, ending at the top with a head 2 to support the brush stick 3. Said head 2 is provided with a through hole 2a, transversal to the longitudinal axis of the bar 1, into which is meant to be inserted the filiform projection 3a of the brush stick 3.

A retention cap 4, provided with two diametrally opposite slots 4a and 4b, is fitted onto the end of the bar 1, over the support head 2, this latter element having a protuberance which slightly projects through the front slot 4a.

Figure 2:
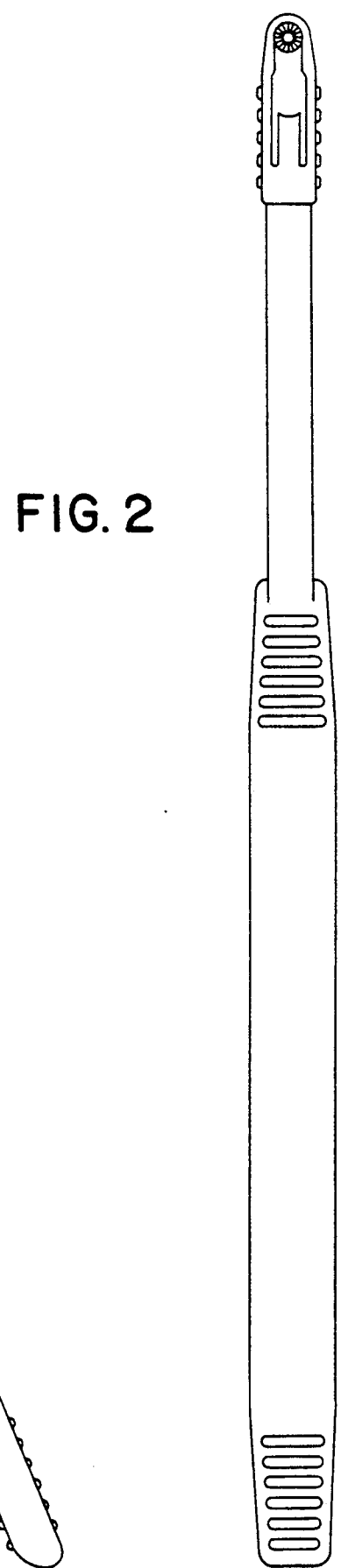

The cap 4 can take up two working positions and, precisely, a position of engagement or release of the brush stick 3 (shown in FIGS. 3, 6 and 4, 7), in which the cap 4 is raised, and a retention or locking position of the brush stick 3 (shown in FIGS. 1, 2 and 5, 8), in which the cap 4 is lowered. Since, the head 2 projects through the slot 4a, the upper and lower parts of the protuberance of said head 2 can act as limit stops in both directions of movement; obviously, the length of the slot 4a, in the direction of the axis of the bar 1, corresponds to the length of the desired stroke.

Two slits 4c (see FIGS. 6 to 8) are moreover provided on the front wall of the cap 4 under the slot 4a, said slits 4c defining a flexible tongue 4d. Because of this arrangement, the cap 4 can be fitted on the head 2 by engaging said head 2 into the open base of the cap 4 and pushing it up: in so doing, the head 2 bears onto the tongue 4d, causing it to deflect outwardly and thus allowing the full insertion of the cap 4. As soon as the head 2 reaches the slot 4a, the tongue 4d is released and springs inwardly, so as to perform the function of a lower limit stop.

The above clearly shows how the brush stick 3 is mounted into the support bar 1:

With the cap 4 in the position of FIG. 3, the projection 3a is inserted into the hole 2a up to bringing the brush stick 3 in contact with the head 2. The projection 3a crosses the hole 2a and then the rear slot 4b, which is now aligned with the hole 2a (position of FIG. 4).

Once the brush stick 3 has been thus positioned, the cap 4 is moved down to the locking position, whereby the rear slot 4b is no longer in alignment with the hole 2a. In performing this movement, the edge of the slot 4b bears onto the projection 3a and bends it downwardly. As clearly shown in FIG. 5, the bent projection 13a is housed into a rear cavity being formed between the head 2 and the inner surface of the cap 4. Since said cavity is formed so as to substantially correspond to the section of the projection 3a, this latter element is firmly locked therein.

To replace the brush stick 3, it is then sufficient to move the cap 4 back into a raised position of release and to slightly pull the stick 3 so as to draw it out of the hole 2a of the head 2.

As can be easily understood, the interdental toothbrush according to the present invention provides the following advantages:

to start with, the cap 4 is in any case locked onto the end portion of the support bar 1 and it is not possible for it to accidentally slip off: in fact, the support head 2—slightly projecting through the front slot 4a—acts as a limit stop for the cap 4 both when it moves down towards the locking position, and when it moves up towards the position of release;

the cap 4 totally surrounds the end portion of the support bar 1 and its shape is rounded both circumferentially and at the end, so as to comprise no sharp edges;

the replacement of the brush stick 3 is extremely easy and practical, while—on the other hand—said brush stick 3 is very firmly retained into its locked position.

It is anyhow understood that the particular embodiment described heretofore, is merely an example, and that other modifications can be introduced, all within reach of a technician skilled in the art, without thereby departing from the protective scope of the following claims for the present invention.

What is claimed is:

1. Interdental tooth-brush, of the type including a support bar (1) having a support head (2) with a transversal hole (2a) at one end, a small brush stick (3) with a filiform projection (3a) apt to engage into said transversal hole (2a), and retention means to fix said projection (3a) of the brush stick (3) into said transversal hole (2a) in an interchangeable manner, characterized in that said retention means comprises:

a cap (4) having two diametrically opposite front and rear slots (4a, 4b), wherein said transversal hole (2a) formed into said support head (2) slightly projects through the front slot (4a) of the cap (4), said cap (4) being fitted onto the one end of the support head (2), axially slidable between a position of release, in which both slots (4a, 4b) are aligned with said transversal hole (2a), and a locking position, in which the rear slot (4b) is axially offset with respect to said hole (2a); in this locking position a cavity being formed between the cap (4) and the support head (2) to house and retain the filiform projection (3a) of the brush stick (3) in a bent position;

wherein a lower edge of the front slot (4a) is formed by a top part of a flexible tongue (4d) formed between two parallel slits (4c) in a front wall of the cap (4).

2. Interdental tooth-brush as in claim 1), wherein an upper edge and, respectively, the lower edge of the front slot (4a) of the cap (4), through which projects a protuberance of said support head (2) of the brush stick (3), are at the same time limit stops for the movement of the cap (4) between said position of release and, respectively, said locking position.

* * * * *